(12) United States Patent
Bangalore et al.

(10) Patent No.: US 7,818,177 B1
(45) Date of Patent: *Oct. 19, 2010

(54) SYSTEM AND METHOD FOR ACCESSING AND ANNOTATING ELECTRONIC MEDICAL RECORDS USING A MULTI-MODAL INTERFACE

(75) Inventors: Srinivas Bangalore, Morristown, NJ (US); Charles Douglas Blewett, Madison, NJ (US); Michael Johnston, Hoboken, NJ (US)

(73) Assignee: AT&T Corp., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/378,560

(22) Filed: Feb. 17, 2009

Related U.S. Application Data

(63) Continuation of application No. 11/788,890, filed on Apr. 23, 2007, now Pat. No. 7,499,862, which is a continuation of application No. 10/329,123, filed on Dec. 24, 2002, now Pat. No. 7,225,131.

(60) Provisional application No. 60/388,847, filed on Jun. 14, 2002.

(51) Int. Cl.
*G10L 21/00* (2006.01)

(52) U.S. Cl. ............... 704/270; 704/275; 600/301; 600/300; 600/483; 600/484; 709/206

(58) Field of Classification Search .......... 704/270, 704/275; 705/104.1, 100; 600/301, 300, 600/483, 484; 382/128; 709/206; 128/925
See application file for complete search history.

(56) References Cited

U.S. PATENT DOCUMENTS

| | | | | |
|---|---|---|---|---|
| 4,809,697 A | * | 3/1989 | Causey et al. ............... 607/31 |
| 4,878,175 A | * | 10/1989 | Norden-Paul et al. .......... 705/2 |
| 4,893,270 A | * | 1/1990 | Beck et al. ................... 700/90 |
| 5,224,206 A | * | 6/1993 | Simoudis ..................... 706/61 |
| 5,447,164 A | * | 9/1995 | Shaya et al. ................ 600/523 |
| 5,452,416 A | * | 9/1995 | Hilton et al. ................ 715/783 |
| 5,473,536 A | * | 12/1995 | Wimmer ..................... 700/90 |
| 5,528,492 A | * | 6/1996 | Fukushima .................... 707/1 |
| 5,544,649 A | * | 8/1996 | David et al. ................. 600/301 |
| 5,549,117 A | * | 8/1996 | Tacklind et al. ............. 600/529 |
| 5,583,758 A | * | 12/1996 | McIlroy et al. ................. 705/2 |
| 5,622,172 A | * | 4/1997 | Li et al. ..................... 600/443 |
| 5,752,917 A | * | 5/1998 | Fuchs ........................ 600/484 |
| 5,776,057 A | * | 7/1998 | Swenson et al. ............ 600/301 |
| 5,785,043 A | * | 7/1998 | Cyrus et al. ................ 600/525 |
| 5,823,948 A | * | 10/1998 | Ross et al. .................. 600/300 |

(Continued)

*Primary Examiner*—Vijay B Chawan

(57) ABSTRACT

A system and method of exchanging medical information between a user and a computer device is disclosed. The computer device can receive user input in one of a plurality of types of user input comprising speech, pen, gesture and a combination of speech, pen and gesture. The method comprises receiving information from the user associated with a medical condition and a bodily location of the medical condition on a patient in one of a plurality of types of user input, presenting in one of a plurality of types of system output an indication of the received medical condition and the bodily location of the medical condition, and presenting to the user an indication that the computer device is ready to receive further information. The invention enables a more flexible multi-modal interactive environment for entering medical information into a computer device. The medical device also generates multi-modal output for presenting a patient's medical condition in an efficient manner.

17 Claims, 5 Drawing Sheets

U.S. PATENT DOCUMENTS

| | | | |
|---|---|---|---|
| 5,950,207 A * | 9/1999 | Mortimore et al. | 707/104.1 |
| 6,424,996 B1 * | 7/2002 | Killcommons et al. | 709/206 |
| 6,611,846 B1 * | 8/2003 | Stoodley | 707/104.1 |
| 7,225,131 B1 * | 5/2007 | Bangalore et al. | 704/270 |

* cited by examiner

FIG. 2
PRIOR ART

S. Jones

202 — { MRN: 44555667  History: Hypertension  Surgeon: Dr. Smith
Age: 80  Diabetes  Operation: CABG
Gender: Female 206 — Swan-Ganz with Cordis

208 — DRIPS

210 — Nitroglycerin: 40 cc/hr
Levophed: 80 cc/hr
Dobutamine: 24 cc/hr
Epinephrine: 10 cc/hr
Inocor: 10 cc/hr 212 — Peripheral IV

214 — BOLUS

204

220 — Peripheral IV

BLOOD — 216

Aterial Line

218

SYSTEM AND METHOD FOR ACCESSING AND ANNOTATING ELECTRONIC MEDICAL RECORDS USING A MULTI-MODAL INTERFACE

PRIORITY APPLICATION

The present application is a continuation of U.S. patent application Ser. No. 11/788,890, filed Apr. 23, 2007, now U.S. Pat. No. 7,499,862, issued Mar. 3, 2009, which is a continuation of U.S. patent application Ser. No. 10/329,123, filed Dec. 24, 2002, now U.S. Pat. No. 7,225,131, issued May 29, 2007, which claims priority to U.S. Provisional Patent Application No. 60/388,847, filed Jun. 14, 2002, assigned to the assignee of the present invention and the contents of which are incorporated herein by reference.

RELATED APPLICATIONS

The present application is related to U.S. patent application Ser. No. 10/217,112, filed Aug. 12, 2002, and U.S. patent application Ser. No. 10/217,010, filed Aug. 12, 2002. The related applications are assigned to the assignee of the present invention and the contents of these applications are incorporated herein by reference.

BACKGROUND OF THE INVENTION

1. Field of the Invention

The present invention relates to multi-modal interfaces and more specifically to a multi-modal interface application for recording and accessing medical information.

2. Discussion of Related Art

Multimedia interactions are being applied to various industries to enhance the exchange of information. One example of this trend is the medical field. Research and development continues on such systems as the "MAGIC" system from Columbia University (MAGIC: Multimedia Abstract Generation for Intensive Care) that uses multi-modal techniques for providing a summary to the intensive care unit after a patient has surgery. The goal of the MAGIC system is to provide a set of tools for producing multimedia briefings that meet the needs of a variety of caregivers, such as specialists and nurses. The MAGIC system employees natural-language generation, knowledge-based graphics generation, and knowledge representation and reasoning systems. See M. Dalai, S. Feiner, K. McKeown, D. Jordan, B. Allen, and Y. Al-Safadi, "MAGIC: An Experimental System for Generating Multimedia Briefings About Post-Bypass Patient Status," *AMIA Fall Symposium*, Washington D.C., October 1996.

FIG. 1 illustrates the MAGIC system architecture 100. The medical databases 102 provide the basic information for the patients. The data server and filter 104 accesses the several medical databases 102 for collecting information about the patient's condition. The databases 102 accessed by the data server 104 include LifeLog database system and a patient clinical database. The data filter 104 selects relevant and important parts of this data and several built-in patient-independent hierarchies (including a Domain Hierarchy and a Concept Hierarchy), infers some new information, and creates a Patient Data Hierarchy used by all subsequent components to represent them.

The general content planner 106 receives the data from the data server and filter 104 and uses the Patient Data Hierarchy and plan library build a Presentation Plan that expresses the high-level Communicative Goals to be accomplished by the Multimedia Briefing. A media allocator 108 chooses one or more media to express each communicative goal in the Presentation Plan. A Medium-Specific Content Planner can expand the Presentation Plan by building detailed plans for the communicative goals assigned to its medium. A Medium-Specific Media Generator uses these detailed plans to generate its portion of the briefing.

The Media Coordinator 110 ensures that the Planners and Generators of different media are consistent with each other. The Media Conductor 116 takes the entire presentation plan and "play" it so that various media are coordinated together, and a single coherent multimedia briefing results. The Constraint Solver 122 provides the central facility for representing the constraints among the different parts of the Presentation Plan and ensures they are mutually consistent.

User Models 124 will represent preferences of individual users and groups of users about the content and format of the Multimedia Briefing. Speech content planner 112, speech generator 114, and graphics content planner 118 and graphics generator 120 are coordinated via the media coordinator 110 and media conductor 116 to present the multimedia medical report for the ICU.

FIG. 2 provides an example of exactly how the MAGIC system presents a patient report. The patient report may be provided to a doctor or a nurse and a button option is presented so that the user can obtain the tailored patient information.

The MAGIC system presents information in a graphical form. FIG. 2 presents the graphical portion of a multimedia report for a "S. Jones." Basic patient information is presented in a heading 202. A three dimensional image of a patient is presented 204. As the report begins, synthetic speech audibly presents the basic information and this portion of the screen is highlighted to let the user (nurse) know that the patient background material is being spoken.

Next, via the synthetic spoken instructions, the MAGIC system gives the patient medical condition and treatment. While the audio is playing, a coordinated presentation of graphics is provided. For example, a text box 210 pops up while the system speaks the composition of the drops 208 given. The text "Swan-Ganz with Cordis" 206 describes a treatment and location on the patient 204 of the treatment. Other text such as "Peripheral IV" 212, 220, "Boles" 214, "Blood" 216, and "Arterial Line" 218 describes further treatment. As the audio portion continues, other pop-up boxes associated with the audio and located near the area of treatment aid in the overall multimedia presentation.

While the MAGIC system presents a helpful multimedia presentation of medical information, the system nevertheless has deficiencies. For example, the MAGIC system receives information from the various databases to generate its presentation. As mentioned above, MAGIC receives data from sources such as a data server, medical databases and patient databases. Other than the normal methods where medical professionals input data to databases, MAGIC provides very little, if any, means of user input prior to the multimedia presentation. Furthermore, it does not appear that there is any opportunity for user input or interaction with the system during the presentation. Therefore, if the information presented to the user (nurse or doctor) is incomplete or the user desires further information—there is no means for interacting effectively with the system.

Physicians and other medical personnel have to quickly record and access large amounts of medical information regarding a patient's condition and the treatments they have received. The medical professionals use this information to record what has happened, to guide further diagnosis and treatment, and also to serve as the basis for billing for treatments and procedures carried out. Currently, the primary method for recording this information is by handwritten shorthand on paper. Some commercial solutions exist which provide the doctor with various forms to fill out in order to indicate the patient's condition. These forms are typically text-based forms. There are also commercial services available where the doctor can call into a central voicemail system and dictate the report of what happened to the patient and the treatments applied. A service provider then transcribes the dictated material and makes it available to the physician. In other situations, when the report is handwritten, often someone else is paid to decode the shorthand specification of the condition and treatment and determine the appropriate billing codes.

SUMMARY OF THE INVENTION

The present invention addresses the deficiencies in the prior art by providing a multi-modal interactive medical application wherein the user can interact with the system. The system and method according to the present invention enables a much more flexible interactive experience for the medical professional. The flexibility of the interaction includes aspects for user input as well as manipulating and controlling multimedia presentations from the system.

According to an embodiment of the invention, a method is provided for a multi-modal exchange of medical information between a user and an electronic medical chart. The electronic medical chart may be any computer device that is arranged to receive user input in a plurality of different types comprising speech, pen, gesture and any combination of speech, pen and gesture. Further, the computer device is arranged to present information in a plurality of system outputs comprising speech, pen, graphics and any combination of speech, pen, text and graphics as well. The method comprises receiving information from the user associated with a medical condition and a bodily location of the medical condition on a patient in one of the plurality of types of user input, presenting in one of the plurality of types of system output an indication of the received medical condition and the bodily location of the medical condition, and presenting to the user an indication that the electronic medical chart is ready to receive further information.

Other embodiments of the invention relate to the computer device for exchanging medical information in a multi-modal fashion and a computer-readable medium storing instructions for controlling a computer device to interact with a user in a multi-modal fashion.

BRIEF DESCRIPTION OF THE DRAWINGS

The foregoing advantages of the present invention will be apparent from the following detailed description of several embodiments of the invention with reference to the corresponding accompanying drawings, in which:

FIG. 2 illustrates a multimedia graphical interface;

DETAILED DESCRIPTION OF THE INVENTION

This disclosure concerns the application of multi-modal interface technology to applications in medical informatics. As mentioned above, there is a need in the medical informatics field for a more convenient and efficient means of exchanging medical information between a user such as a doctor or a nurse and a computer device. An aspect of the present invention provides a method for annotating and accessing electronic medical records such as patient charts using multi-modal input and output. Another aspect of the invention is that in addition to handwriting recognition, the invention provides for gesture recognition of gestures made to indicate locations on a body (using circles, points, arrows, and the like). Medical records often have to be created and accessed in mobile environments. These records include the emergency room, ambulances, and mobile field settings during disaster response and warfare.

Figure 1:
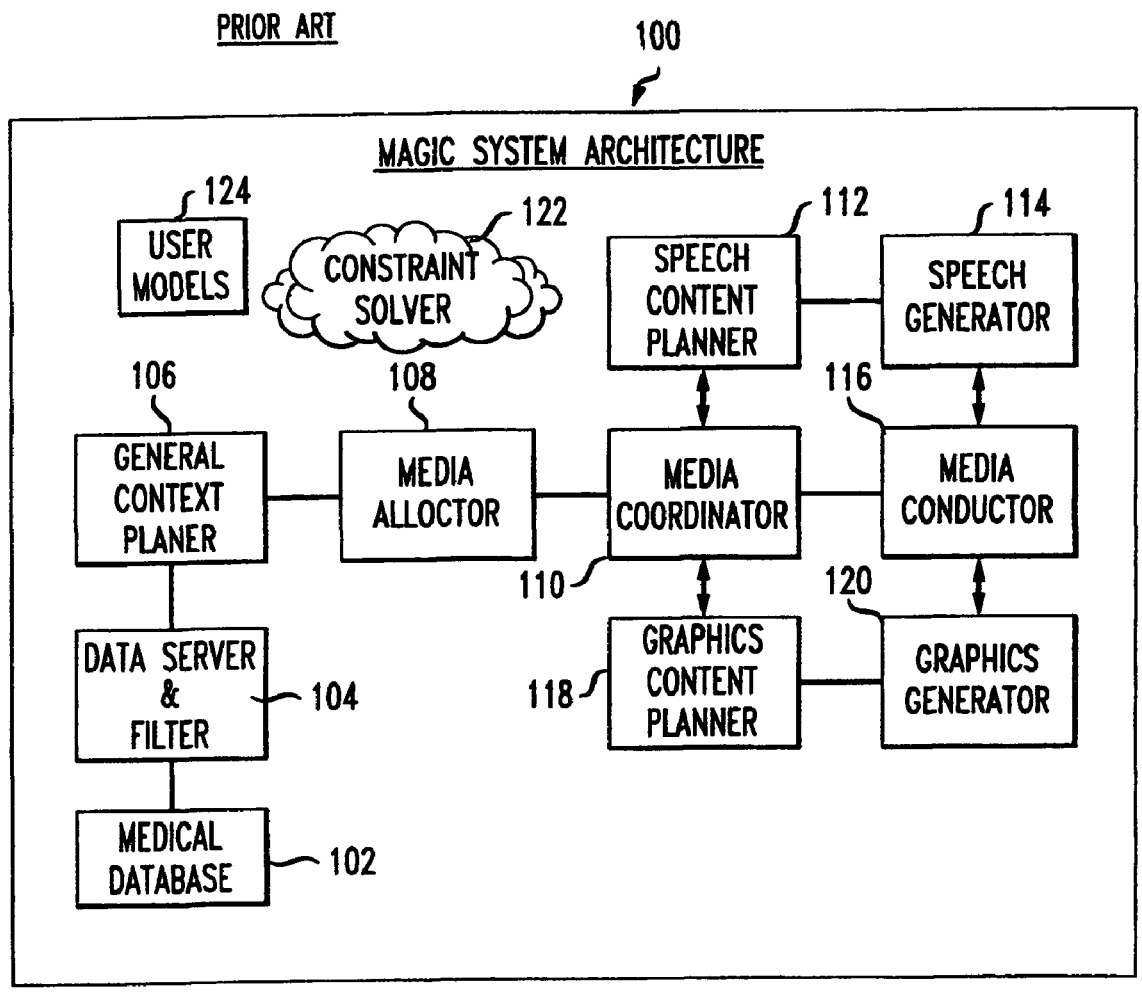
FIG. 1 illustrates a prior art architecture for a multimedia presentation system.
Figure 3:
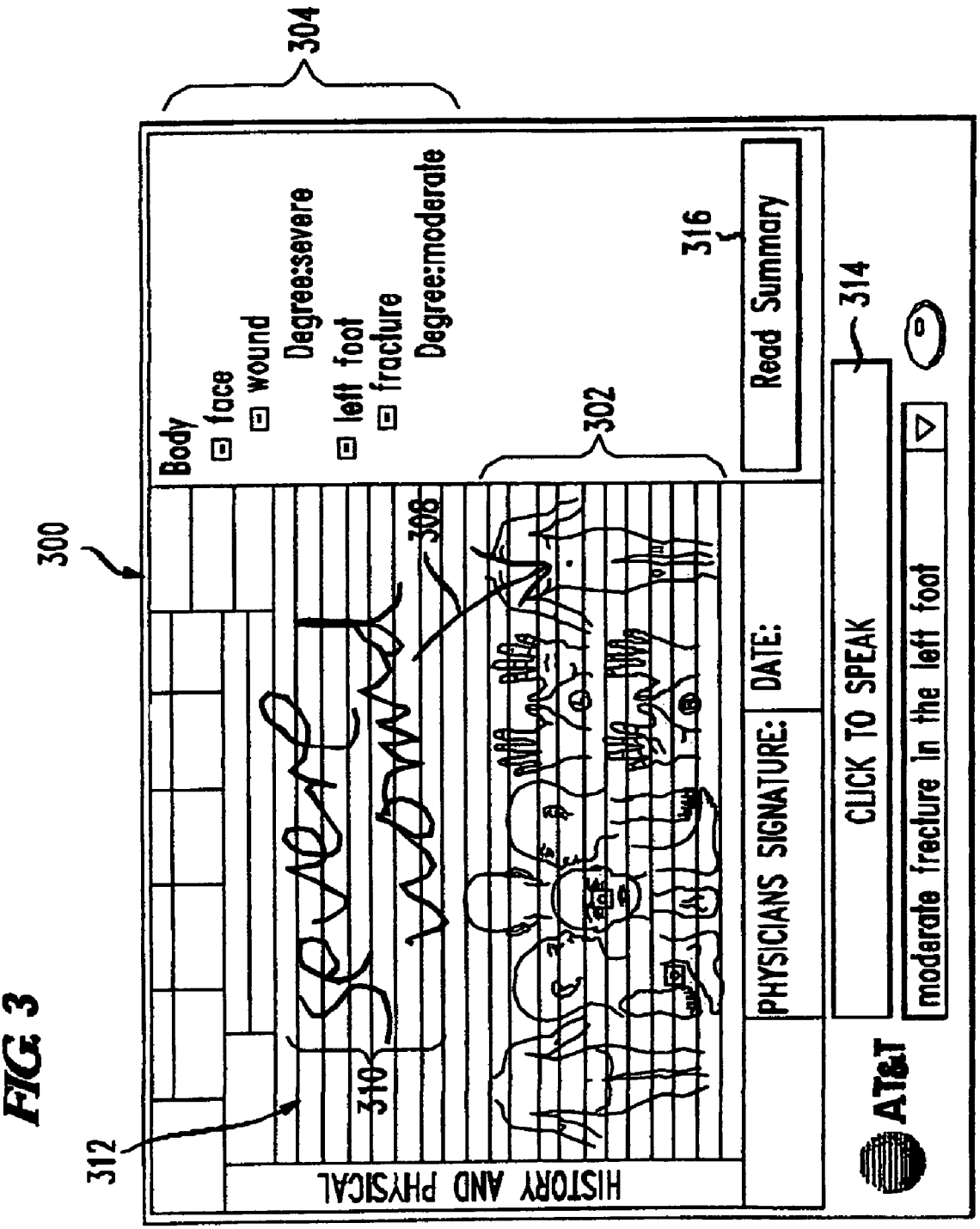
FIG. 3 illustrates an exemplary embodiment of the invention.

In order to address the challenges of converting handwritten or voice recorded instructions from a doctor into a medical record, the inventors of the present invention provide an electronic medical chart on a mobile computing device. An example embodiment of this invention is an "ECHART" 300 shown in FIG. 1. The ECHART device displays schematic graphics of sections of the human body 302 and displays a tree structure 304 indicating the various different conditions and treatments. The interface 300 is enabled with electronic ink 308 so that the user can indicate body locations by circling or pointing at them. The user may also write handwritten words 310 on the touch-sensitive display. In this regard, there are known techniques for handwriting recognition. Presented as background to the body part sections 302 and the handwriting and gesture 308 is an example patient history and physical 312 that help to guide the user in making notes. An advantage of the tree structure 304 and its graduated detail of information as you move further into the tree is that it may provide the user or reader with a means of accessing more detailed information. For example, the tree structure 304 in FIG. 3 shows a left foot fracture that is moderate. The tree structure 304 may include links to more detailed information. A digital picture of the wound may be stored and brought up for a user to actually view the wound instead of a drawing of the location of the wound. X-rays may be incorporated wherein the user cannot only see a digital picture of the wound but also X-rays of the fracture. The ultimate benefit of the ECHART example is to provide a multi-modal and easy access to medical information.

The ability to provide gestural input with graphics of a body as a background schematic enables the doctor/medical personnel to give far more detailed spatial information. For example, the doctor may indicate dimensions of an incision and/or a region where tissue was removed using gestural input. The doctor may be able to indicate the extent of bruising or other damage using gestural input that conveys more information than a written explanation.

The system is also speech enabled. The user can select the click-to-speak button 314 on the interface and provide spoken input. The flexibility of the user input is enabled by software that receives each of the different types of user input, whether it be speech, pen or handwriting, gestures or any combination of inputs, and generates a lattice to determine what the multi-modal meaning is. The applications incorporated above include details and other examples of the finite-state-machine techniques that lead to multi-modal input understanding. Accordingly, no further details need to be provided here.

The ECHART interface provides the user with tremendous flexibility in their input. In general, one of the main tasks in using an electronic medical record is to annotate the record with specifications of the patient's condition and treatment. In this example embodiment, the user can make three kinds of annotations: wounds, fractures, and drugs administered. Note the points 316 and 318 that correspond to the tree 304. Points 316 and 318 highlight the medical information in the tree, which is a severe facial wound and a moderate fracture of the left foot.

There is any number of possible combinations of input. For example, a physician might indicate bruising or discoloration, where surgical procedures were performed and so on. In order to make an annotation, the user is free to choose to use speech, pen, gestures or a multi-modal combination of the modes. As an example, consider the wound to the foot. The user can specify the annotation wholly in speech by clicking on the bar 314 and saying "A moderate fracture to the left foot." The user could also indicate the wound by using pen only by writing 'severe' and 'wound' and circling the location of the wound on the left foot. The same annotation can also be made using a synchronized combination of speech and pen, for example the user can say "severe wound" and circle the location in question or draw an arrow to the bodily location. The system applies speech recognition, gesture recognition, and handwriting recognition to the user inputs and uses a multi-modal finite state transducer to combine them and work out what the user is trying to indicate.

The system responds by marking the location of the annotation using a small yellow graphical widget 316 or 318. Other kinds of graphical images may be employed to confirm the multi-modal input. A confirmation dialog may also be employed if the system is unsure or a threshold of confidence is not met. Such a dialog could be in the form of a widget that pops up on the screen asking the user to confirm the interpretation of the multi-modal input. The annotation also appears in the graphical tree control 304 on the display. If the user clicks on the widget 316 or 318 a graphical panel comes up which allows them to alter and further specify the annotation. This could be used also to enter billing codes in one application of this technology.

The widgets are clickable and open up to reveal a graphical user interface (GUI) that allows the user to fine-tune or correct the specification of the condition or treatment. For example, the present invention provides support for a type of interaction where the user employs multi-modal commands to indicate the condition in general terms then is provided with a carefully tailored GUI that enables the user to provide the specific details.

A read summary button 320 also is presented to the user to make available a more detailed summary of the injuries than is available in screen 300 including the hierarchical summary 304. All of these graphical widgets and information may be programmed in any known web-type programming language. Other computer programming languages may also be used.

Figure 4:
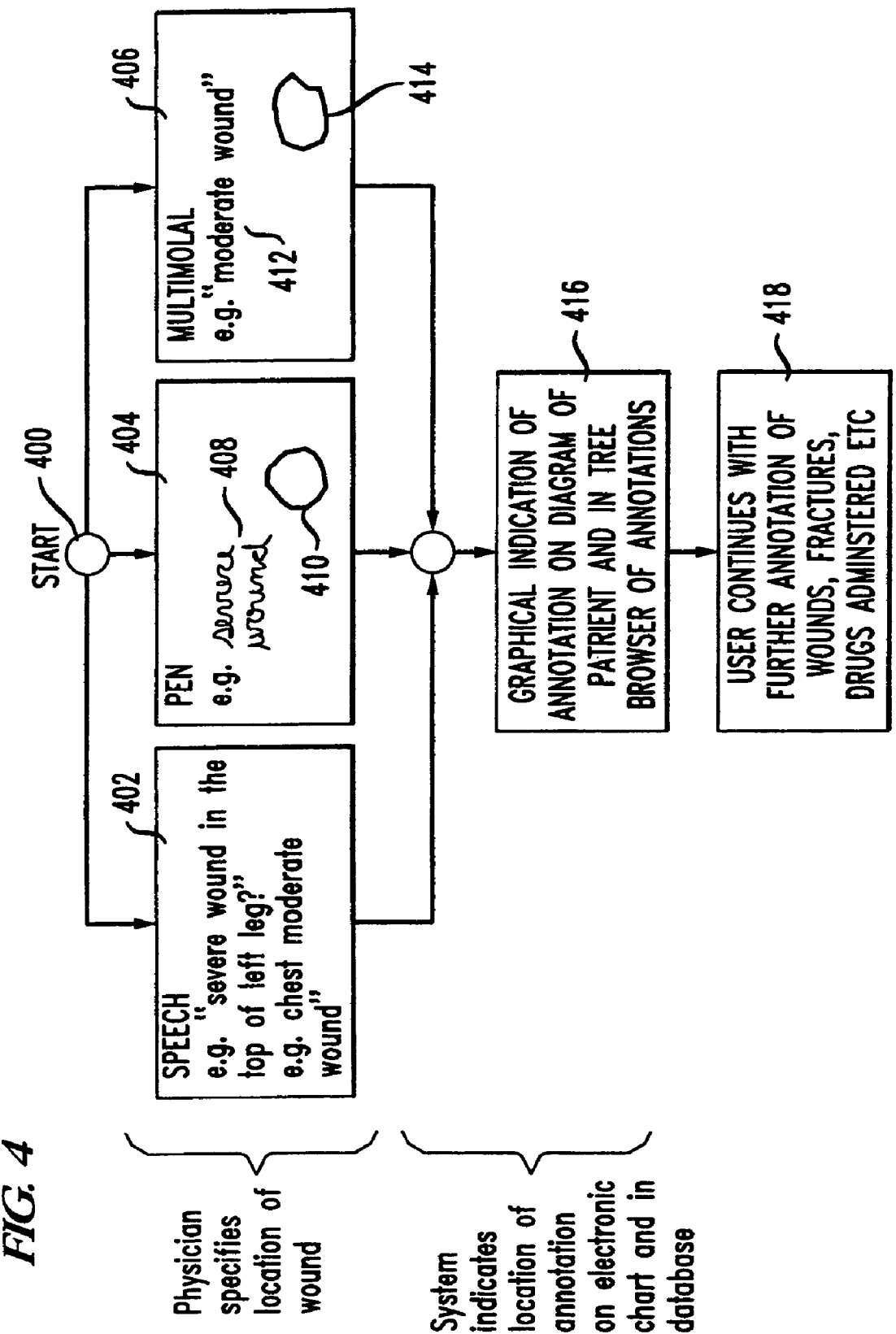
FIG. 4 illustrates a method of interacting with a user according to an aspect of the invention.

The flexible interface process for specifying the location of wounds is represented as flowchart in FIG. 4. This flowchart illustrates an example of how a user may provide input to the system for wounds but the approach of course could apply to recording information regarding fractures, medicine provided and what dosages and where, or any other kind of patient treatment. The flowchart provides examples and shows the interface process. At the starting point 400, the user is typically viewing a screen on a computer device such as a handheld device. The screen may be similar to that shown in FIG. 3 with an open medical record.

Step 402 illustrates speech input to the computer device. In the example, the user states "severe wound in the top of left leg" or "chest—moderate wound." The user (nurse or doctor) typically needs to provide a description of what happened (wound, fracture or drugs administrated) and where it happened, such as upper leg, arm, chest, etc. Therefore, in one mode, the user can state all the information by saying "epinephrine 10 mg in the left arm" or "light fracture in the right arm."

An alternate means of user input is shown in box 404 where the user combines handwriting "severe wound" 408 and a gesture 410 that circles the location of the severe wound (see FIG. 3 for body sections that are available for the user to circle). Yet another mode of input combines speech and gesture. This mode is illustrated by box 406, wherein the user states "moderate wound" 412 and gestures 414 the location of the wound.

For example, the user may say "epinephrine 10 milligrams in the left arm" or alternatively write "epinephrine—90 mg" and circle the left arm. The user may say "we administered 90 milligrams of epinephrine here" and circle the left arm with the pen. The user could also just specify the drug name and location using speech, pen or a combination and then click on an annotation widget and select the dosage from a menu. The system allows for a combination of multi-modal speech/pen interaction with more traditional graphical interaction.

The system receives the input in any of the modes, interprets the multi-modal or uni-modal input and provides a graphical indication of the annotation on a diagram of the patient and in a tree browser of annotations 416. Step 416 involves providing the graphical indication of the annotation on the electronic chart and in a database or the annotation tree. For example, if the user is specifying a wound in a leg, the system will receive the multi-modal input and present a confirmation of that by indicating a location in the leg with a "wound" annotation. Then the user immediately knows if the system properly understood the input.

Finally, the user can continue 418 to input further medical information on the patient in a similar manner to continue annotating wounds, fractures or other drugs administered. In this manner, the user can input all the treatment into the system in a convenient, multi-modal or uni-modal manner.

Once the user completes inputting the information, the computer device must be capable of conveniently and efficiently presenting the patient data. The system utilizes multi-modal output for presentation of information to the user. In a preferred embodiment of the invention, the system provides a multi-modal presentation summarizing the patient's condition and treatment to the user. The patient summary is activated by hitting the READ SUMMARY button 316 on the right of the interface shown in FIG. 3. For each annotation that has been made the system coordinates highlighting the relevant annotation widget 316, 318 with spoken output describing the conditions or treatment. For example the system will highlight the left arm and say "We administered 90 mg of epinephrine to the left arm".

Figure 5:
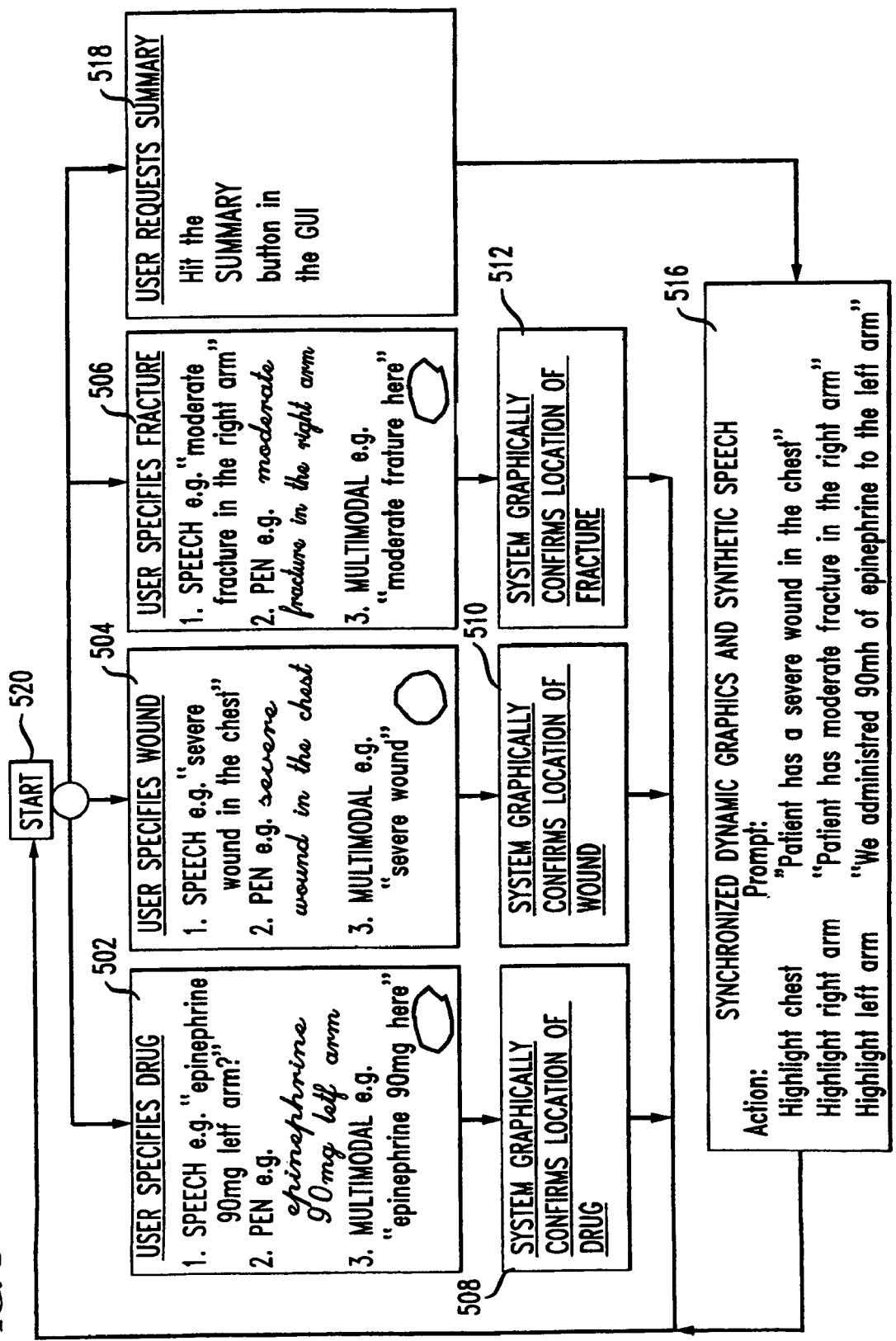
FIG. 5 illustrates another aspect of interacting with the user according to the invention.

FIG. 5 shows how this functionality connects into the annotation mechanism and provides an overview of the overall capability of the prototype. At point 500, the user is ready to input information into the computer device or to request a summary for the patient. Step 502 summarizes the user input for drugs in a speech-only mode, pen-only mode and a multi-modal input. Step 504 illustrates similar input for a wound, and step 506 illustrates further kinds of input for a fracture. In each case they can use speech, pen, or multi-modal input.

The system responds 508, 510, 512 by indicating the location and updating the tree on the right. The system then goes back to start state and the user can continue to make further annotations. The user may be ready at point 500 to review a summary of the patient's condition. Then, the user selects the "READ SUMMARY" button 514. The system generates a multi-modal presentation incorporating the various different annotations made up until that point. Box 516 illustrates the synchronized and dynamic graphics and synthetic speech. The system may highlight the chest and prompt: "Patient has a severe wound in the chest." Other examples are provided in box 516. One potential use for the summary mechanism is to quickly provide an update to a second physician or nurse who has to treat the patient.

The primary use of this technology is for making annotations and accessing information on the mobile device. However the same approach could be applied in a desktop consol or display built into a counter. It could also be used on a wall size display. The approach provides a high degree of flexibility provided to the user for both providing input and receiving output.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, mini-computers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Although the above description may contain specific details, they should not be construed as limiting the claims in any way. Other configurations of the described embodiments of the invention are part of the scope of this invention. For example, although the above-preferred embodiments relate to medical devices, the basic principles of a multi-modal input and output can apply in other fields such as power-line analysis or auto mechanics. Accordingly, the appended claims and their legal equivalents should only define the invention, rather than any specific examples given.

We claim:

1. A method executed in connection with a mobile computer device for inputting medical data, the method comprising:
    receiving in the mobile computer device from a user a plurality of user inputs associated with a medical condition and a bodily location of the medical condition on a patient, the plurality of user inputs including a synchronized combination of at least two modes of user inputs;
    in the mobile computer device, combining the user inputs to determine an indication of the received medical condition and the bodily location of the medical condition; and
    presenting from the mobile computer device to the user an output of the indication.

2. The method of claim 1, wherein the step of combining the user input modes is performed using a multi-modal finite state transducer in the mobile computer device.

3. The method of claim 1, wherein the output of the indication includes graphics of a body.

4. The method of claim 1, wherein the output of the indication includes a tree structure with graduated information detail pertaining to the indication.

5. The method of claim 1, wherein the plurality of user inputs includes speech recognition.

6. The method of claim 1, wherein the plurality of user inputs includes gesture.

7. The method of claim 1, wherein the plurality of user inputs includes a pen and tablet.

8. The method of claim 1, further comprising the step of displaying on the mobile computer device an electronic medical chart.

9. The method of claim 1, wherein the step of presenting to the user an output of the indication includes presenting through synthesized speech.

10. The method of claim 1, wherein the step of presenting to the user an output of the indication includes presenting through text.

11. The method of claim 1, wherein the step of presenting to the user an output of the indication further comprises highlighting a patient image on a display screen indicating the bodily location of the medical condition and indicating the medical condition.

12. A mobile computer device for inputting medical data, comprising:
    a plurality of user interfaces for receiving inputs from the user associated with a medical condition, the interfaces capable of receiving user inputs in at least two user input modes used by a user in a synchronized combination; and
    a multi-modal recognition module using a finite-state machine to build a single meaning representation from the synchronized combination of user inputs.

13. The mobile computer device of claim 12, further comprising:
 at least one user interface for presenting an indication of the received medical condition.

14. The mobile computer device of claim 13, wherein the indication of the received medical condition includes a bodily location of the medical condition.

15. The mobile computer device of claim 13, wherein the user interface for presenting an indication of the received medical condition is further for presenting a hierarchical tree summary of the received information associated with the medical condition and a bodily location of the medical condition.

16. The mobile computer device of claim 12, further comprising:
 a user interface for presenting to the user an indication that the computer device is ready to receive further information.

17. The mobile computer device of claim 12, wherein the plurality of user interfaces for receiving inputs comprises at least one interface selected from the group consisting of voice recognition, pen and tablet and gesture.

* * * * *